United States Patent [19]

Kato et al.

[11] Patent Number: 4,457,622
[45] Date of Patent: Jul. 3, 1984

[54] SCREW INSPECTION DEVICE

[75] Inventors: Michio Kato; Hayao Takahashi, both of Yokosuka; Hidekazu Hoshino, Yokohama, all of Japan

[73] Assignee: NHK Spring Co., Ltd., Yokohama, Japan

[21] Appl. No.: 343,351

[22] Filed: Jan. 27, 1982

[51] Int. Cl.³ .............................................. G01N 21/88
[52] U.S. Cl. ................................ 356/237; 250/223 R; 250/560; 209/586
[58] Field of Search ............. 356/237, 73; 250/223 R, 250/560, 572; 209/539, 576, 586, 587, 920, 934

[56] References Cited

FOREIGN PATENT DOCUMENTS

55-70704  5/1980  Japan ..................................... 356/237

Primary Examiner—David C. Nelms
Assistant Examiner—L. A. Dietert
Attorney, Agent, or Firm—Frishauf, Holtz, Goodman & Woodward

[57] ABSTRACT

A screw inspection device of the invention has a screw transfer mechanism for transferring a screw through a predetermined transfer path, a sensor for performing predetermined measurements of the screw during transfer thereof, a timing signal transmitter for generating a timing signal every time the screw reaches the sensor, a comparator for generating an acceptance/non-acceptance signal representing the measurement results from the sensor every time the timing signal is received, a sorting signal generator for generating a sorting signal corresponding to the acceptance/non-acceptance signal when the corresponding screw reaches the end of the transfer path, and a sorter for classifying the screws into defective and nondefective screws.

7 Claims, 14 Drawing Figures

SCREW INSPECTION DEVICE

BACKGROUND OF THE INVENTION

The present invention relates to a screw inspection device having a parts feeder and transfer means for sequentially transferring screws through a predetermined transfer path while maintaining the screws in a predetermined posture.

Figure 1A:
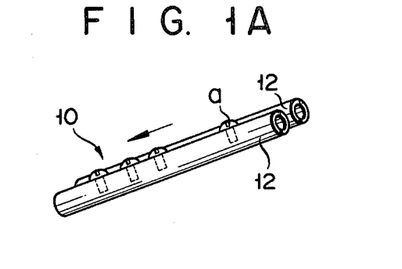
FIGS. 1A and 1B are perspective views, from two different directions, of a conventional roller type sorter which is widely used for a conventional screw inspection device.
Figure 1B:
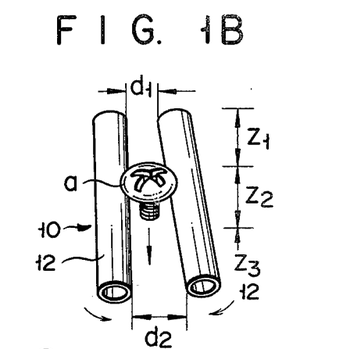

With the development of automatic assembly devices, automatic screw fasteners have been recently used widely. When an automatic screw fastener is fed with defective screws, the automatic screw fastener is rendered inoperative. Therefore, the operation of the automatic screw fastener must be temporarily stopped to remove the defective screws or to perform other repair operations. This adversely affects the related manufacturing line and causes a tremendous damage. In order to avoid the above problem, various inspection devices are incorporated into the automatic screw fastener. A roller type sorter 10 which is employed in a conventional screw inspection device is shown in FIGS. 1A and 1B. The roller type sorter 10 transfers a screw a and sorts in accordance with the diameter of the screw head. FIGS. 1A and 1B show the basic members for explaining the structure and function of the roller type sorter. As shown in these figures, the roller type sorter 10 has two rollers 12 of the same shape. The two rollers 12 are disposed so that extended lines of their axes cross with each other. The ends which are close to the crossing point of the extended lines are disposed lower than the ends which are away from the crossing point. A gap between the ends of the rollers 12 which are close to the crossing point, is narrower than that between the other ends thereof. In particular, symbol d1 denotes the gap between the upper ends and symbol d2 denotes the gap between the lower ends, in which gap d1 is narrower than gap d2. The two rollers 12 rotate so that opposing surfaces of the rollers 12 move upward, that is, the rollers 12 rotate in opposite directions. Gaps d1 and d2 and the length of the rollers 12 are selected in accordance with the diameter of the screw head to be inspected. When the screw a is fed to and supported by the circumferential faces of the upper ends of the rollers 12, the head of the screw a is supported by the rollers 12 while the screw a is transferred to the lower ends thereof. When a screw whose head diameter is smaller than the tolerance is transferred from the upper ends, this screw drops from an upper zone Z1 between the rollers 12 while being transferred. When a screw whose head diameter is within the tolerance is transferred, this screw drops from an intermediate zone Z2 between the rollers 12. Further, when a screw whose head diameter is larger than the tolerance, the screw drops from a lower zone Z3 between the rollers 12. In this manner, the screws a are classified into three types: the screw whose head diameter is smaller than, within, and larger than the predetermined tolerance. As apparent from the above description, this roller type sorter 10 is a device for inspecting the head size of the screws a with simple construction and easy handling.

Figure 2:
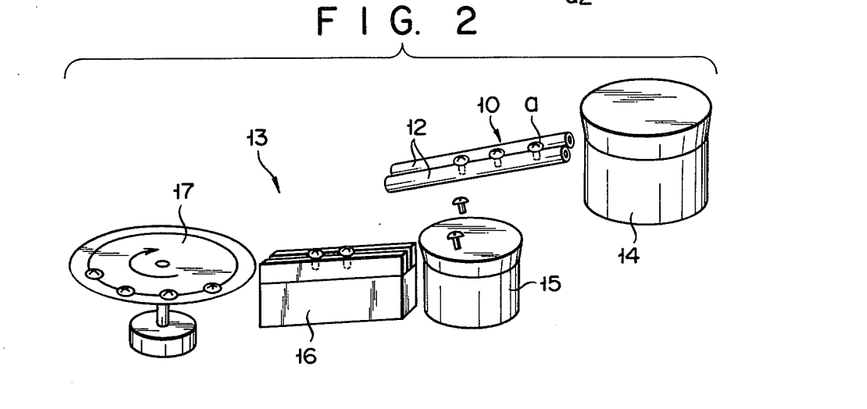
FIG. 2 shows the conventional screw inspection device which uses the roller type sorter of FIG. 1.

FIG. 2 shows a conventional screw inspection device which is capable of performing various inspections on the screw, incorporating other sensors (not shown) and including the roller type sorter 10. The screw inspection device 13 of FIG. 2 comprises the roller type sorter 10, a first parts feeder 14 which feeds the screw a to the roller type sorter 10, a second parts feeder 15 which stacks the screw a the head of which has a diameter within the tolerance and which is dropped from the intermediate zone Z2, a linear feeder 16 which is disposed in the screw feeding side of the second parts feeder 15, a rotating table 17 which is disposed in the screw feeding side of the linear feeder 16, and a plurality of inspection units (not shown) such as various transfer mechanisms and sensors which are arranged around the rotating table 17. The sensors, for example, are sensors for detecting the shank length of the screw a, the presence or absence of threads of the screw a, and detecting whether or not plating is performed well. The screw inspection device with the above structure works effectively. However, many problems must be solved. For example, the smooth transfer of the screw a from the linear feeder 16 to the rotating table 17 is not well accomplished. Further, the transfer operations between other transfer mechanisms are not efficiently and smoothly accomplished. The rough transfer operation results in mechanical trouble. When the screw inspection device 13 breaks down, the operation thereof must be interrupted in order to repair a broken part, thus shortening the operation time. Further, in addition to the roller type sorter 10, the two parts feeders 14 and 15, the linear feeder 16, the rotating table 17 and the like are required, resulting in a complex structure with a high manufacturing cost. Further, every time the kind of screw changes, the roller type sorter must be adjusted, resulting in inconvenience.

SUMMARY OF THE INVENTION

It is an object of the present invention to provide a screw inspection device which automatically performs various desired inspections and sorting with simple structure, low manufacturing cost and good operability.

In order to achieve the above object of the present invention, there is provided a screw inspection device having a parts feeder which supplies a screw and a transfer means for sequentially transferring the screw which is fed from the parts feeder along a predetermined transfer path while the screw is maintained in a predetermined posture, comprising a plurality of sensors which are disposed along the transfer path, which perform predetermined measurements for the screw which has been transferred to the transfer path and which output a measurement signal which indicates measured results; a timing signal transmitter which outputs a predetermined timing signal every time a screw reaches a sensor; a comparator which is disposed for each sensor, in which a predetermined tolerance is set and which receives the measurement signal and the timing signal, said comparator comparing the measurement signal and the tolerance in response to the timing signal so that a predetermined acceptance/non-acceptance signal is output from the comparator when the measurement signal is within or outside the tolerance; a sorting signal generator which counts the number of acceptance/non-acceptance signals supplied from the sensors, which stores the acceptance/non-acceptance signals and the order in which the screws corresponding to the acceptance/non-acceptance signals pass through the transfer path, and which outputs a sorting signal corresponding to the acceptance/non-acceptance signal when the sum of the acceptance/non-acceptance signals which are generated from one of the sensors which is disposed closest to an end of the transfer path, reaches the order; and a sorter which receives the sorting signal and which sorts screws which are fed from the end of the transfer path into non-defective screws and defective screws.

With the screw inspection device of the above structure, the sorting is not performed by the diameter of the head before transferred to the transfer path as described with reference to the conventional device. Therefore, the screw is fed only once from the parts feeder to the transfer means to be sorted. In the conventional device of FIG. 2, the screw is sequentially transferred four times through many machines, that is, from the first parts feeder 14 to the roller type sorter 10, from the roller type sorter 10 to the second parts feeder 15, from the second parts feeder 15 to the linear feeder 16, and from the linear feeder 16 to the rotating table 17, thus resulting in dropping and clogging. However, interruption of the device, according to the present invention, as a whole, due to clogging is reduced considerably.

The path on which the screw is transferred is extremely simple in construction as compared with the conventional device. Various sensors are disposed along the way among the paths as described above. Thus, various inspections and measurements are performed while the screw is being transferred so that a mechanism such as a rotating table for a special path need not be used. The screw inspection device according to the present invention is made simple and compact, resulting in low costs for the screw inspection device itself and in savings on installation and maintenance.

In a preferred embodiment of the screw inspection device according to the present invention, a vibration type transfer device is used as the transfer means which transfers a screw by causing it to jump. In this case, a intermediate viscoelastic body is fired to the upper surface of the feeder main body and a thin support body is fixed to the upper surface of the intermediate viscoelastic body, a screw is placed directly on the thin support body. The feeder main body performs a reciprocal movement with vibration in the oblique direction. In this manner, a screw which jumps to advance and is dropped on the thin support body, rests on the thin support body within a short period of time, so that the screw is measured while being transferred. Therefore, in the screw inspection device according to the present invention, a benefit such as easy and precise measurement is accomplished.

DETAILED DESCRIPTION OF THE PREFERRED EMBODIMENTS

Figure 3:
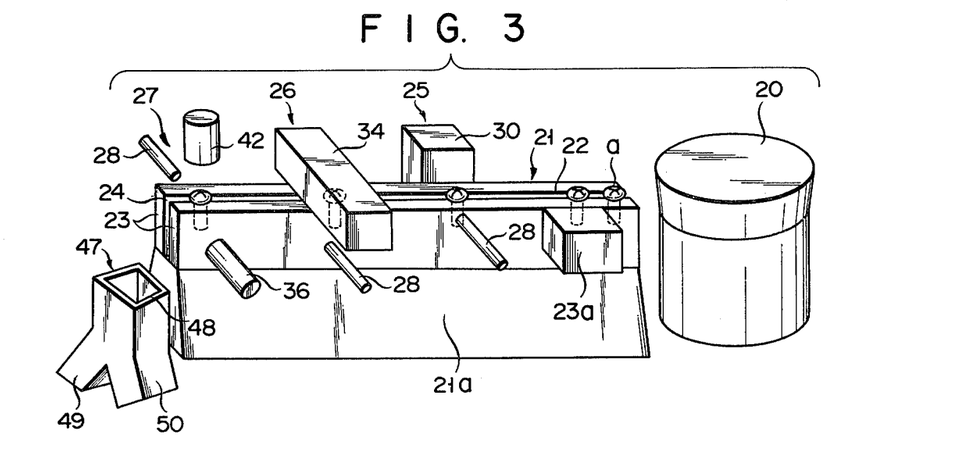
FIG. 3 is a perspective view of a screw inspection device according one embodiment of the present invention.

A screw inspection device according to one embodiment of the present invention will be described with reference to FIGS. 3 to 7. A parts feeder 20 which is used for a screw inspection device of FIG. 3 is the same as the parts feeder which is conventionally used. Screws a, the heads of which face upward, are sequentially fed and transferred to a transfer means 21. The transfer means 21 has a pair of side walls 23 which stand upright from a base table 21a and which oppose each other substantially parallel to each other with a groove 22 defined therebetween. The groove 22 has a width which is less than the diameter of the head of the screw a and which is greater than the diameter at the shank of the screw a. The screws a, fed from the parts feeder 20, are sequentially transferred downstream (to the left in FIG. 3) such that the heads thereof face upward and the shanks thereof extend therefrom within the groove 22. In order to transfer screws a in this manner, many measures may be taken. For example, the side walls 23 may be slightly inclined from the upstream side to the downstream side. A vibrator 23a may be mounted to the side walls 23 to provide vibrations to the side walls 23. Other suitable means may be used to obtain the same results.

As described hereinabove, screws a are sequentially transferred along a transfer path 24 defined by the groove 22 of the transfer means 21. Therefore, if a desired number of inspection stages, three in the figure, 25, 26 and 27, are arranged along the transfer path 24, the screws a may receive required inspections while they are being transferred by the transfer means 21. Every time screw a reaches the respective inspection stages 25, 26 and 27 during transfer, a predetermined timing signal is generated from a timing signal transmitter 28 which is incorporated for each inspection stage. The timing signal transmitter 28 may comprise a light-emitting element (not shown) which emits light toward the screw a and a light-receiving element for receiving light reflected by the screw a to generate the predetermined timing signal. Alternatively, the timing signal transmitter 28 may utilize emitted light in place of the reflected light which is interrupted by the screw. Furthermore, the timing signal transmitter 28 may utilize other suitable, known principles.

Figure 4:
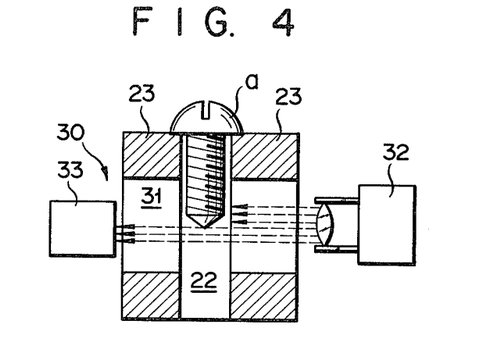
FIG. 4 is a view for explaining the principle of measurement of a shank length sensor of FIG. 3.

The inspection items of the screws a assigned to the respective inspection stages 25, 26 and 27 may be selected according to the purpose of inspection. For example, the inspection stage 25 has a shank length sensor 30 which generates a signal representing the shank length of the screw a. The shank length sensor 30 has a light-emitting element 32 and a light-receiving element 33. The light-emitting element 32 and the light-receiving element 33 are arranged so as to communicate with each other by means of through holes 31 in the side walls 23. The screws a are supported at the upper ends of the side walls 23 such that the shanks thereof extend in the groove 22 defined between the side walls 23. The light-receiving element 33 comprises a plurality of photodiodes which are arranged at a predetermined pitch parallel to the shanks of the screws a. A signal corresponding to the number of photodiodes which did not receive light due to the presence of the screws a is generated by the light-receiving element 33. Therefore, if the distance between the light-receiving element 33 from the tops of the side walls 23 is correctly set in advance, the shank length of the screw a can be calculated from the results obtained from the shank length sensor 30. In comparison with an analog-type sensor which is widely used for conventional screw inspection devices, which generates an electric signal representing the amount of light blocked by the screw, the light-receiving element 30 of the present invention is less subject to adverse effects of changes in environmental factors, and measurements of the shank length may be performed with high precision and reliability. Instead of forming through holes 31, it is also possible to prepare the side walls 23 from a transparent material.

Figure 5A:
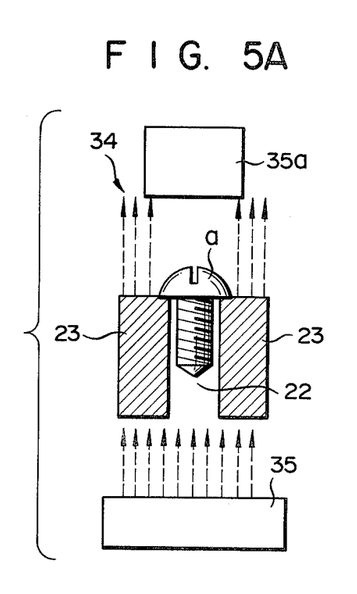
FIGS. 5A and 5B are views for explaining the principle of measurement of a head diameter sensor of FIG. 3.
Figure 5B:
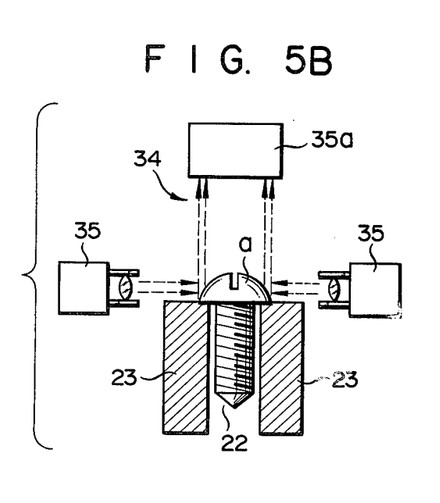

The inspection stage 26 shown in FIG. 3 has, in this embodiment, a head diameter sensor 34 which measures the diameter of the head of the screw a. As shown in FIG. 5A, the side walls 23 which oppose each other are made of a transparent material, and have a light-emitting element 35 and a light-receiving element 35a which oppose each other above and below the side walls 23. The light-receiving element 35a has a plurality of photodiodes which are arranged at a predetermined pitch in a two-dimensional manner. The photodiodes which do not receive light from the light-emitting element 35 due to the presence of the head of the screw a do not generate output signals. Therefore, the output signals from the photodiodes are sequentially scanned in a predetermined direction to obtain output signals of an array of photodiodes corresponding to the maximum number of zero outputs. In this manner, the diameter of the head of the screw may be calculated from these output signals. FIG. 5B shows a head diameter sensor 34 of a type different from that shown in FIG. 5A. In this case, the light emitted by the light-emitting elements 35 which are arranged at both sides of the head of the screw a illuminates both sides of the head of the screw a, and the light reflected from the head of the screw a is received at the light-receiving element 35a. The light-receiving element 35a has a plurality of photodiodes which are arranged at a predetermined pitch in a two-dimensional manner. The light reflected by the head of the screw a becomes incident on these photodiodes, and the diameter of the head of the screw a is calculated from the output distribution of the photodiodes. Depending upon the shape of the head of the screw a, the light-emitting element and the light-receiving element as in the shank length sensor 30 described with reference to FIG. 4 may be used. In this case, the light is radiated on the head of the screw a along the surfaces of the side walls 23, and the photodiodes of the light-receiving element do not receive the light reflected by the head of the screw in a pattern when it is viewed perpendicularly to the shaft of the screw. Therefore, the diameter of the head, which is the longest distance along the horizontal line of the shadow pattern may be obtained from the output distribution of the photodiodes in the similar manner as in the case of the shank length.

Figure 6A:
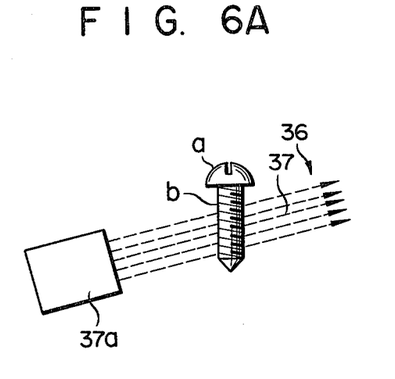
FIGS. 6A and 6B are views for explaining the principle of detecting operation of a thread sensor of FIG. 3.
Figure 6B:
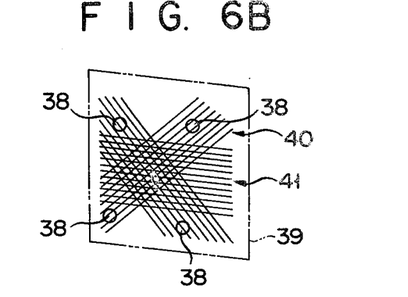

A thread sensor 36 for sensing the threaded condition of the screw a is arranged in the inspection stage 27 in the embodiment shown in FIG. 3. The thread sensor 36 has, as shown in FIG. 6A, a laser-device which radiates a laser beam 37 which circumscribes a threaded portion b of the screw a, and a light-receiving element 38 for receiving the laser beam which is diffracted by the threaded portion b. The laser beam 37 is projected on a screen 39. If threads are not formed at the portion b, a diffraction image 41 of the light diffracted by the portion b includes a number of parallel lines which extend substantially perpendicularly to the shaft of the screw. However, if the threads are formed at the portion b, a diffraction image 40 is determined by the lead angle of the threads and includes parallel lines which extend in a direction different from that of the diffraction image 41. In order to distinguish between these two diffraction images, the light-receiving element 38 is arranged at a position outside the diffraction image 41 and within the diffraction image 40. Then, by detecting the output signal from the light-receiving element 38, the presence or absence of the threaded portion b may be detected. In comparison with the conventional method, that is, the analog method according to which the light is projected on the threaded portion b and the intensity of reflected light is converted into an electric signal to detect the presence or absence of the threaded portion b, the arrangement of the embodiment of the present invention is advantageous in that the thread sensor 36 need not be adjusted according to the condition of the threaded portion and the detection of the threaded portion may be performed with high reliability. A plating sensor 42 for discriminating the quality of plating of the screw a is also arranged at the inspection stage 27 in addition to the thread sensor 36. The plating sensor 42 generates a signal representing the intensity of the laser beam reflected by the screw a. The presence or absence of plating, or the quality of the plating of the screw a may be discriminated by comparing the signal representing the intensity of the reflected light with a predetermined tolerance.

Figure 7:
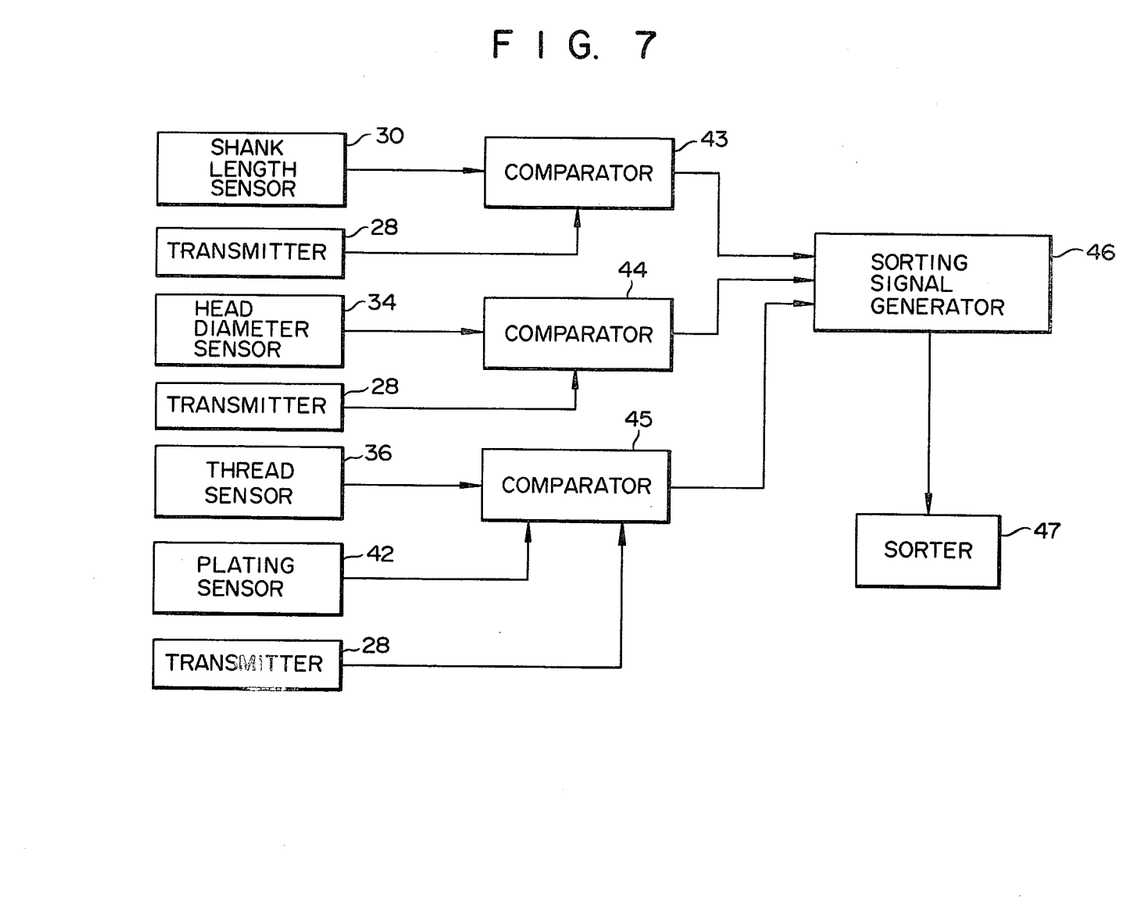
FIG. 7 is a block diagram, partially showing the screw inspection device of FIG. 3, for explaining the mode of operation which brings a screw from various sensors to a sorter.

The four kinds of sensors 30, 34, 36 and 42 described above are connected, as shown in the block diagram in FIG. 7, to first, second and third comparators 43, 44 and 45, together with the timing signal transmitter 28 which are incorporated for the respective sensors. The outputs from the comparators 43, 44 and 45 are supplied to a sorting signal generator 46, the output of which is supplied to a sorter 47.

A reference value of the shank length of the screw a, and the tolerance, that is, the allowable error, are preset in the first comparator 43 in advance. In response to a timing signal supplied from the associated timing signal transmitter 28, the first comparator 43 starts operating to compare the signal representing the measurement obtained from the shank length sensor 30 with the tolerance. When the data of measurement falls within the tolerance, the first comparator 43 generates a predetermined acceptance signal.

The tolerance of the diameter of the head of the screw a is preset in the second comparator 44 in advance. In response to a timing signal supplied from the associated timing signal transmitter 28, the second comparator 44 compares the signal representing the measurement obtained by the head diameter sensor 34 with the tolerance. As a result of the comparison, if the measurement falls within the tolrance, the second comparator 44 generates a predetermined acceptance signal.

The tolerance of the plating degree of the screw a is preset in the third comparator 45. In respone to a timing signal supplied from the associated timing signal transmitter 28, the third comparator 45 starts operating to compare the signal representing the measurement with the tolerance. When the measurement falls within the tolerance, the third comparator 45 generates a predetermined acceptance signal. The sorting signal generator 46 counts the number of acceptance signals from each of the comparators 43, 44 and 45, so as to store the acceptance/non-acceptance signals and the order of the screws corresponding to the acceptance/non-acceptance signals which pass the transfer path 24. Each time the sum of the acceptance signals generated from the sensor 36 which is the closest to the end of the transfer path reaches the corresponding ordinal number, the sorting signal generator 46 generates a sorting signal corresponding thereto.

The sorter 47 has an inlet port 48 for receiving, as shown in FIG. 3, the screw a which is transferred from the transfer path 24, a switching means (not shown) operative in response to the sorting signal from the sorting signal generator 46, a nondefective screw deliver path 49 and a defective screw exhaust path 50 which communicate with the inlet port 48. When the sorting signal is supplied to the switching means from the sorting signal generator 46, the switching means operates. Then the nondefective screws among the screws a introduced through the inlet port 48 are transferred to a predetermined location through the nondefective screw deliver path 49, and the defective screw is transferred to a predetermined location through the defective screw exhaust path 50.

According to the arrangement described above, the screws a are subjected to predetermined inspections at the inspection stages 25, 26 and 27 while they are sequentially transferred along the transfer path 24 defined by the groove 22 and a pair of side walls 23. Therefore, the screw inspection device of the present invention is significantly simple in construction as compared with the conventional device 13 as shown in FIG. 2. The screw inspection device of the present invention has various advantages. For example, only one parts feeder 20 (FIG. 3) is required. The roller type sorter 10 or the rotating table 17 as shown in FIG. 2 are not required. The cost of the overall device may be significantly reduced. Handling and maintenance of the device is easy. Since the shank length sensor 30 is of digital type, the measurement precision and reliability are higher than those obtainable with the analog type shank length sensor. Since the thread sensor 36 utilizes the diffraction of the laser beam, control is easier than the conventional sensor which utilizes the reflected light, also resulting in an advantage that higher precision and reliability may be obtained.

The embodiment described above is only an example, and various other modifications and changes may be made within the scope of the present invention. For example, the number of inspection stages, the kinds of items to be inspected at the respective inspection stages, the arrangement and order of the inspection stages, and the sensing principle of the respective sensors may be changed. Furthermore, if needed, the transfer path 24 may be curved instead of straight. The arrangement of the parts feeder 20, the sorter 47 and so on, or whether or not to incorporate them at all may be changed according to the type of inspection required.

Figure 8:
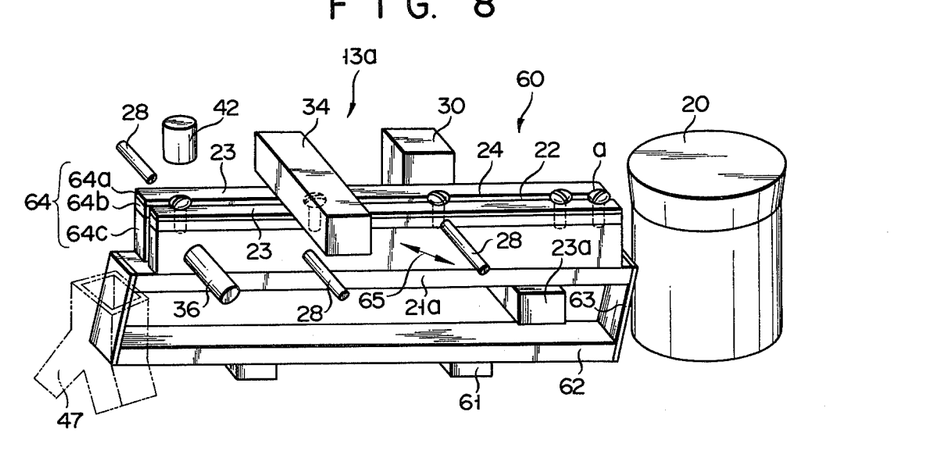
FIG. 8 is a perspective view of an embodiment which uses a vibration type transfer means in place of the transfer means of FIG. 1.

FIG. 8 shows a screw inspection device 13a which uses a vibration type transfer device 60 which is different from that shown in FIG. 3. In the transfer device 60, a feeder main body 64 is supported through leaf springs 63 on a base body 62 which is fixed to legs 61 placed on the floor. The feeder main body 64 consists of a thin support body 64a, an intermediate viscoelastic body 64b, and a base body 64c. The lower end of the base table 21a mounting the feeder main body 64 is fixed through leaf springs 63 to the base body 62. Therefore, when the leaf springs 63 are mounted to the base body 62 to be inclined to the right as shown in FIG. 8, and the vibrator 23a provides vibrations to the feeder main body 64, the feeder main body 64 is vibrated and moved as indicated by an arrow 65 so that it is higher toward the left and lower toward the right. Since the amplitude of the vibration of the feeder main body 64 is relatively small, the vibrations may be regarded as reciprocal linear vibrations along the direction indicated by the arrow 65. The thin support body 64a is usually made of a material which has abrasion resistance and suitable elasticity and which allows sliding movement thereon, such as quenched ribbon steel. If desired, the thin support body 64a may be made of a nonmetallic material depending upon the operating conditions. The intermediate viscoelastic body 64b may be made of a soft material having a shock absorbing characteristic, such as rubber or foamed material. In special cases, the intermediate viscoelastic body 64b may be an adhesive material which bonds the thin support body 64a and the base body 64c.

Figure 9:
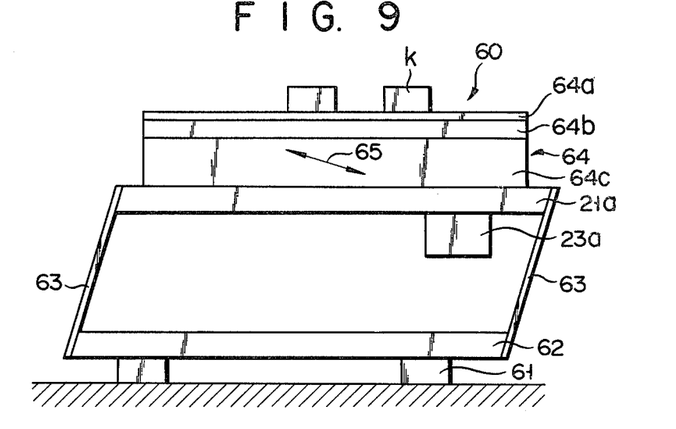
FIG. 9 is a front view showing the structure of the vibration type transfer device of FIG. 8.
Figure 10:
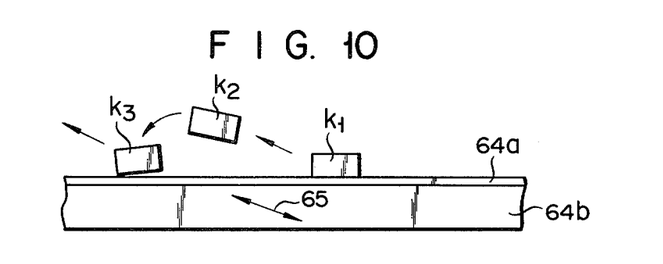
FIG. 10 is a view for explaining the mode of operation of the device of FIG. 8.
Figure 10A:
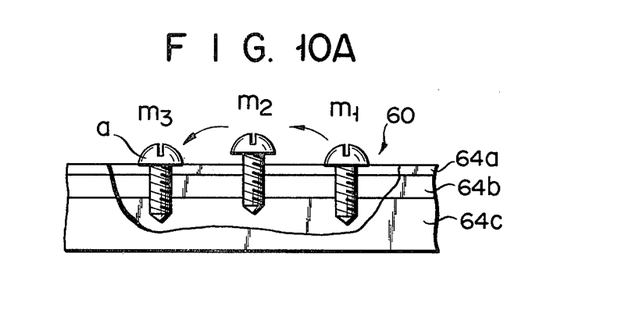
FIG. 10A is a view for explaining the mode of operation in which a screw is transferred in accordance with the mode of operation of FIG. 10.

The principle of displacement of the screw to the left will be explained with reference to FIGS. 9 and 10 when the feeder main body 64 reciprocates with vibrations in the direction indicated by the arrow 65. FIG. 9 is an enlarged view of the vibration type transfer device 60 alone. In these figures, a rectangular parallelepiped k is drawn in place of a screw a. When the feeder main body 64 is driven in the direction indicated by the arrow 65, the rectangular parallelepiped k jumps from the position indicated by k1 in the figure to the position indicated by k3 through the position indicated by k2. Therefore, if the vibrations are provided continuously, even if the upper surface of the feeder main body 64 is substantially horizontal, the rectangular parallelepiped k sequentially moves to the left. The displacement of the rectangular parallelepiped k as described above is performed by the jump of the rectangular parallelepiped k. However, when the rectangular parallelepiped k reaches the feeder main body 64, the rectangular parallelepiped k does not receive the forward force but the force in the opposite direction. Therefore, it is preferable that the impact which the rectangular parallelepiped k may receive when it reaches the feeder main body 64 may be reduced, so that the rectangular parallelepiped k may settle quickly and the inspection may be completed quickly. In the case wherein the screw a is inspected while it is being transferred as in FIG. 8, the screw a jumps from the position at which its shank extends into the groove 22 and its head is supported by the thin support body 64a to the upper left position. Thus, the screw a moves to the left and drops on the feeder main body 64 such that the reaction is suppressed by the thin support body 64a and the intermediate viscoelastic body 64b. The movement of the screw a is schematically shown in FIG. 10A. Referring to FIG. 10A, the screw jumps from m1 to m2, and from m2 to m3, that is, it moves to the left because of the vibrations. The pitch of the screw is shown as emphasized with respect to the height of the jump of the screw. Therefore, the screw a is setted on the feeder main body 64 quickly, so that the various inspections as described above may be performed during this settling period.

In the screw inspection device shown in FIG. 8, the vibration type transfer device 60 is used, so that the reaction generated when the screw a reaches the feeder main body 64 is significantly suppressed by the intermediate viscoelastic body 64b and the thin support body 64a. Therefore, it becomes possible to vibrate the feeder main body 64 stronger than with the conventional screw inspection device which does not use the members 64a and 64b, so that the reliable transfer and the reliable inspection of the screws may be guaranteed.

What we claim is:

1. A screw inspection device comprising:
   a parts feeder which supplies a screw;
   transfer means for sequentially transferring the screw which is fed from said parts feeder along a predetermined transfer path while the screw is maintained in a predetermined posture;
   a plurality of sensors disposed along said transfer path, each performing a predetermined measurement for the screw which has been transferred to said transfer path and output a measurement signal which indicates measured results;
   a plurality of timing signal transmitters each of which outputs a predetermined timing signal every time a screw reaches said sensors;
   a comparator which is disposed for each of said sensors, in which a predetermined tolerance is set and which receives the measurement signal and the timing signal, said comparator comparing the measurement signal and the tolerance in response to the timing signal so that a predetermined acceptance/non-acceptance signal is output from said comparator when the measurement signal is within or outside the tolerance;
   a sorting signal generator which counts the number of acceptance/non-acceptance signals supplied from said sensors, which stores the acceptance/non-acceptance signals and the order in which the screws corresponding to the acceptance/non-acceptance signals pass through said transfer path, and which outputs a sorting signal corresponding to the acceptance/non-acceptance signal when a sum of the acceptance/non-acceptance signals which are generated from one of said sensors which is disposed closest to an end of said transfer path; reaches a corresponding ordinal number; and
   a sorter which receives the sorting signal and sorts the screws which are fed from the end of said transfer path into non-defective screws and defective screws.

2. A device according to claim 1, wherein said transfer means comprises:
   a base body;
   a pair of side walls which stand substantially upright from said base body with a groove defined therebetween, said groove having a width which is smaller than a head diameter of the screw and which is greater than a diameter at a shank of the screw, upper sides of said side walls being inclined downward along a direction of movement of the screw; and
   vibrating means for vibrating said side walls.

3. A device according to claim 2, wherein said transfer means comprises:
   an intermediate viscoelastic body which is mounted to upper sides of said side walls;
   a thin support body which is mounted on said intermediate viscoelastic body; and
   spring means for supporting said base body from below and for reciprocating said base body with vibrations so that said base body may be inclined to be at a higher level at the downstream side in a direction of movement of the screw and at a lower level at the upstream side thereof.

4. A device according to claim 3, wherein said thin support body is made of quenched ribbon steel.

5. A device according to claim 3, wherein said intermediate viscoelastic body is made of rubber.

6. A device according to claim 3, wherein said intermediate viscoelastic body is made of a foamed material.

7. A device according to claim 3, wherein said intermediate viscoelastic body is made of an adhesive.

* * * * *